(12) United States Patent
Earthman et al.

(10) Patent No.: US 7,221,445 B2
(45) Date of Patent: May 22, 2007

(54) METHODS AND APPARATUS FOR DETECTING AND QUANTIFYING SURFACE CHARACTERISTICS AND MATERIAL CONDITIONS USING LIGHT SCATTERING

(75) Inventors: James C. Earthman, Irvine, CA (US); Vladimir B. Markov, Irvine, CA (US); James D. Trolinger, Costa Mesa, CA (US); Derek Dunn-Rankin, Irvine, CA (US); Benjamin D. Buckner, Irvine, CA (US)

(73) Assignee: MetroLaser, Inc., Irvine, CA (US)

( * ) Notice: Subject to any disclaimer, the term of this patent is extended or adjusted under 35 U.S.C. 154(b) by 378 days.

(21) Appl. No.: 10/823,385

(22) Filed: Apr. 12, 2004

(65) Prior Publication Data

US 2005/0036135 A1 Feb. 17, 2005

Related U.S. Application Data

(60) Provisional application No. 60/462,359, filed on Apr. 11, 2003.

(51) Int. Cl.
*G01N 21/88* (2006.01)
(52) U.S. Cl. .................... 356/237.2; 356/600
(58) Field of Classification Search ........ 356/600–625, 356/630–634, 639, 237.2; 250/559.22, 559.23, 250/559.29, 559.31, 225
See application file for complete search history.

(56) References Cited

U.S. PATENT DOCUMENTS 3,986,160 A * 10/1976 Turner ............... 367/7
4,664,514 A * 5/1987 Corby, Jr. ............... 356/36

(Continued)

OTHER PUBLICATIONS

Brede et al., "Brittle Crack Propagation in Silicon Single Crystals," J. Appl. Phys., vol. 70, No. 2, Jul. 15, 1991, pp. 758-771.
Buerkle et al., "Rapid Defect Detection by Laser Light Scattering," Materials Evaluation, Jun. 1992, pp. 670-677.
Diaz et al., "Optical Measurement of the Plastic Zone Size in a Notched . . . ," Optics and Lasers in Engineering, vol. 35, 2001, pp. 325-333.

(Continued)

*Primary Examiner*—Sang H. Nguyen
(74) *Attorney, Agent, or Firm*—MacPherson Kwok Chen & Heid LLP

(57) ABSTRACT

A system for quantifying surface characteristics detects and quantifies characteristics of a surface of an object. For example, the system may quantify changes in surface roughness without contacting the specimen and without requiring precise temporal or spatial stability. The system may also quantify the evolution or progression of a particular characteristic of a surface, such as a defect, a slipband, a crack, a microcrack, a pit, a damage feature, corrosion, a contour change, an impact crater, a change in residual stress, and so on. The system may include an energy source, a detector section, and a process section. The energy source transmits a source signal to the surface of the object. The source signal is specularly reflected and/or scattered by the surface to yield one or more received signals. The detector section receives the received signal and, in turn, provides a detector signal indicative of the received signal. The processor applies an algorithm to the detector signal to quantify an evolution in one or more characteristics of the surface.

32 Claims, 11 Drawing Sheets

U.S. PATENT DOCUMENTS

| | | | |
|---|---|---|---|
| 5,293,216 A * | 3/1994 | Moslehi | 356/600 |
| 5,377,002 A * | 12/1994 | Malin et al. | 356/237.2 |
| 5,426,506 A * | 6/1995 | Ellingson et al. | 356/369 |
| 5,608,527 A | 3/1997 | Valliant et al. | |
| 5,708,506 A * | 1/1998 | Birang | 356/600 |
| 5,812,269 A * | 9/1998 | Svetkoff et al. | 356/602 |
| 5,978,091 A * | 11/1999 | Jann et al. | 356/613 |
| 6,392,749 B1 * | 5/2002 | Meeks et al. | 356/634 |
| 6,862,096 B2 * | 3/2005 | Vaez-Iravani et al. | 356/600 |

OTHER PUBLICATIONS

Valliant et al., "Instrument for On-line Monitoring of Surface . . . ," Opt. Eng., vol. 39, No. 12, Dec. 2000, pp. 3247-3254.

Zhao et al., "Characterization of Pitting Corrosion in Aluminum . . . ," Applied Physics Letters, vol. 73, No. 17, Oct. 26, 1998, pp. 2432-2434.

* cited by examiner

METHODS AND APPARATUS FOR DETECTING AND QUANTIFYING SURFACE CHARACTERISTICS AND MATERIAL CONDITIONS USING LIGHT SCATTERING

CROSS-REFERENCE TO RELATED APPLICATION

The present application claims priority under 35 U.S.C. 19(e) on U.S. Provisional Application for Patent Ser. No. 60/462,359 filed Apr. 11, 2003, the entire disclosure of which is incorporated herein by reference.

STATEMENT REGARDING FEDERALLY SPONSORED RESEARCH

This invention was made with government support under Contract Number DAAD10-02-C-0007 awarded by the U.S. Army applied Technology directorate (AMCOM) to Metro-Laser, Inc. The government has certain rights in the invention.

BACKGROUND OF THE INVENTION

1. Field of the Invention

The present invention relates to techniques and methods for detecting and quantifying surface characteristics and material conditions using light scattering.

2. Description of the Related Art

Detecting and monitoring fatigue damage is needed for preemptive failure repair or replacement of critical components in engineering systems. A macroscopic crack does not generally manifest until very late in the life of the component high cycle fatigue (HCF) conditions. However, surface structural changes and micro-cracks can occur much earlier on the surface and could possibly be used as a precursor for fatigue crack formation that leads to catastrophic failure. Therefore, it is of great importance to develop methods to quickly detect localized deformation and micro-cracking early in the fatigue life, well in advance of micro-crack coalescence and macroscopic crack growth.

Early in the fatigue process, dislocations in crystalline solids migrate to give rise to localized deformation, which in turn leads to micro-crack initiation and eventual failure. Crack formation typically occurs very late in fatigue life (within the last 20%) under high cycle fatigue conditions and, therefore, early determination of fatigue and estimation of remaining life requires the detection of dislocation structures as they impinge on the surface of the specimen. Optical visualization of precursor dislocation structures prior to crack formation is generally not possible for engineering components. However, in materials that have moderate to high surface residual stresses, the initial formation and movement of dislocations can reduce surface residual stress. The relationship between cyclic loading and a decrease in residual stress has been observed and reported by many researchers. For example, substantial relaxation of residual stresses during fatigue loading has been observed using x-ray diffraction techniques. The relaxation of residual stresses by 30% in mild steel under fatigue loading conditions was also measured using high sensitivity Moiré interferometry. Similarly, a laser light scattering technique was shown to efficiently detect not only micro-cracks, but also a reduction in surface roughness on wire specimens that were subjected to high cycle fatigue conditions. This change in roughness was attributed to cyclic relaxation of large residual stresses at the surface that resulted from the wire drawing process.

Microcrack formation occurs relatively early in the life of samples under low cycle fatigue (LCF) conditions. The number of microcracks that develop prior to the formation of the primary crack also increases with the greater imposed strain amplitude under LCF conditions. Monitoring the gradual increase in the microcrack density early in the life of an LCF specimen can provide an accurate prediction of fatigue life. Although this monitoring can be performed using surface replication techniques, a less time intensive method is needed to make microcrack monitoring practical for life assessment of components in service.

Various techniques have been proposed for the optical measurement of surface roughness and defect detection including laser ultrasonic, laser Doppler vibrometry, interferometry, and scattered light scanning.

In view of the foregoing, there is a need in the art for methodology and system that utilize scattered light detection so as to be more reliable, simpler in operation, and have the lowest cost to implement when compared to conventional system.

BRIEF SUMMARY OF THE INVENTION

The present invention provides methods and techniques for detecting and quantifying characteristics of a material surface such as defects, microcracks, slipbands, cracks, pits, damage, contour changes, residual stress, impact craters, corrosion, erosion, pits and other surface properties of interest by detecting and analyzing light scattered from a beam that has been focused on or near and scanned over the surface. In one embodiment, the light beam is scanned over the surface. In an alternate embodiment, the light beam is stationary and the surface itself moves in such a manner that the scanning function is achieved. As an example of this latter case, the beam is focused on a rotating specimen and the light scattered from the specimen varies as the surface scans under the light beam.

In a number of embodiments, methods and apparatus for monitoring surface changes utilize the light scattered from the surface of an object under a fatigue load that is illuminated by a focused scanning laser beam. The temporal and spatial evolutions of the characteristics of the scattered light are sensitive to deformation of crystal boundaries, formation of dislocations (slipbands), changes in features supported by residual stresses, as well as initiation and growth of microcracks early in the fatigue life. These processes occur well in advance of crack coalescence and growth; thus, the invention may serve as an effective detector of fatigue damage precursors.

According to another aspect, a system of monitoring a surface characterizes a surface state by analyzing temporal changes or bursts in the detected, scattered light signal, associated with variations in the light scattering properties of defects, microcracks, slipbands, etc. One of the analyzing methods uses a defect frequency parameter that is determined to minimize computer memory requirements and data processing time. The defect frequency may be defined as the frequency of light scattering bursts having an intensity above a predetermined threshold.

One example of an application of the system is to monitor fatigue damage (for example, in a turbine blade) by scanning a laser beam along component in situ and during periodic interruptions of the cyclic loading. In this embodiment, the system of the invention functions as an in situ monitor that focuses light on a component and collects scattered light as defects, cracks, and other surface characteristics pass under the focused light beam. In this implementation the device may serve, for, example as a continuous health-monitoring tool for rotating machinery. In such an embodiment, the system characterizes fatigue damage precursors on the surface of turbine components. In particular, a rapid rise in the mean defect frequency may correspond to surface relief features that correspond to localized deformation along grain boundaries that intersect the surface in the areas of greatest stress. The presence of this surface relief can be attributed to the presence of relatively soft precipitate free zones along the grain boundaries that preferentially deform under fatigue loading conditions leading to the formation of microcracks.

Another application of the system is the noninvasive interrogation and inspection of airframe components that are subject to fatigue damage. Defects due to fatigue do not generally manifest themselves until very late in the life of the component, just prior to failure; however, surface structural changes and micro-cracks occur first at the surface, and can be used as a precursor to defect detection. Accordingly, the system may be utilized to detect and monitor the damage due to cycling fatigue is critical for preemptive failure and health monitoring.

According to still another aspect of the invention, a method is provided for measuring changes in surface morphology of an object, such as a turbine rotor, that are related to fatigue loading conditions, impending crack formation, or foreign object damage.

Other features and advantages of the present invention will become apparent to those skilled in the art from a consideration of the following detailed description taken in conjunction with the accompanying drawings.

DETAILED DESCRIPTION OF THE INVENTION

Figure 1:
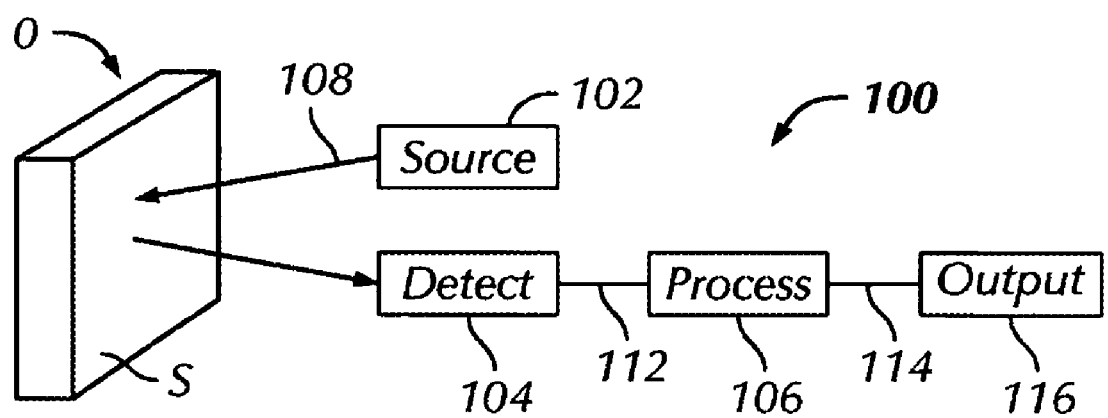
FIG. 1 illustrates a system for quantifying a characteristic of a surface of an object.

A representative embodiment of a system 100 for quantifying surface characteristics is illustrated in FIG. 1. As will be discussed in detail below, the system 100 and associated methodology may detect and quantify characteristics of a surface S of an object O. For example, the system 100 may quantify changes in surface roughness without contacting the specimen and without requiring precise temporal or spatial stability. In other embodiments, the system 100 may quantify the evolution or progression of a particular characteristic of the surface S, such as a defect, a slipband, a crack, a microcrack, a pit, a damage feature, corrosion, erosion, a contour change, an impact crater, a change in residual stress, and so on.

According to a number of embodiments, the system 100 may include a transmit section including an energy source 102, a receive section including a detector section 104, and a process section including a processor 106. The energy source 102 transmits a source signal 108 to the surface S of the object O. The source signal 108 is specularly reflected and/or scattered by the surface S to yield one or more received signals 110. The detector section 104 receives at least a portion or number of the received signals 110 and, in turn, provides a detector signal 112 indicative of the received signal 110. The processor 106 receives the detector signal 112 and applies an algorithm thereto to quantify an evolution in one or more characteristics of the surface S.

For the purposes of this description, the received signal may include portions of the source signal 108 that are specularly reflected by the surface S, scattered by the surface S, or both. In addition, if the object O enables at least partial transmittance of the source signal 108 (e.g., glass for a laser), then a portion of the source signal 108 may be forward scattered (as opposed to back scattered) by the object O as a received signal 110.

In some of the embodiments, the energy source 102 may transmit the source signal 108 over time, either continuously or discretely with periods of time between transmitting the source signals 108. In the latter embodiments, the period of time may be of any length, from a few seconds to years. The processor 106 may then apply an algorithm to the detector signal 112 to quantify time-varying or temporal changes in the characteristic of the surface S. In addition, the processor 106 may also apply an algorithm to quantify spatial changes in the characteristic of the surface S. The processor 106 may then provide a characteristic signal 114 to an output device 116, such as a computer for further processing. A number of properties of the energy source 102, such as incidence angle, polarization, and wavelength, may be varied to improve processing performance.

Figure 2:
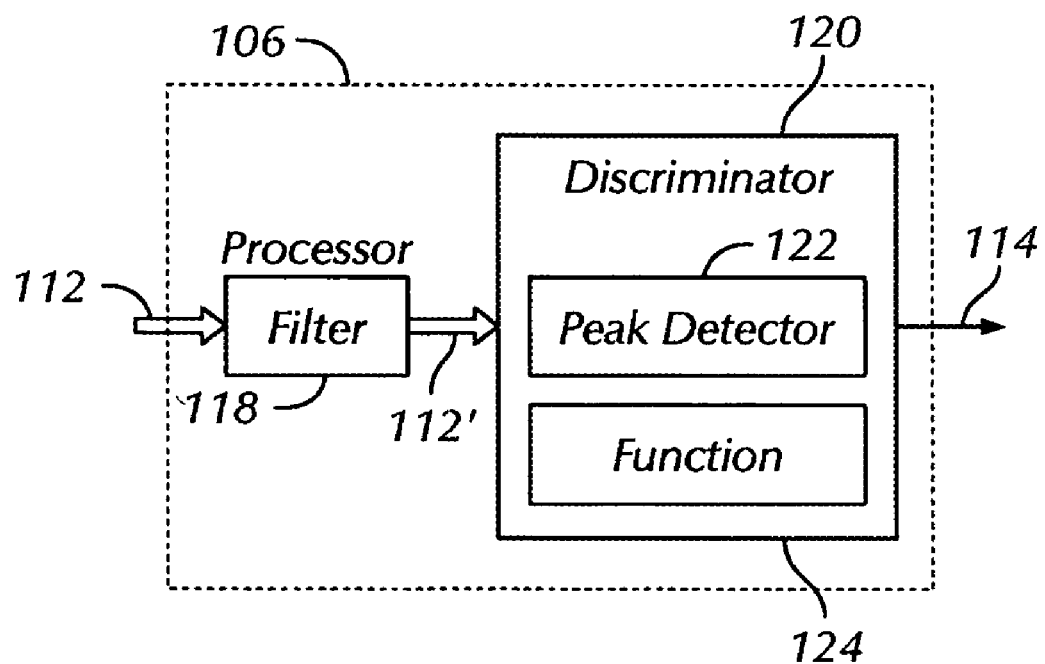
FIG. 2 illustrates a process section of the system.

Referencing FIG. 2, in a number of embodiments the processor 106 may include a filter 118 and a discriminator 120. The filter 118, which may include a bandpass filter, wavelet filter, or other type of filter, may receive the detector signals 112 and provide a corresponding plurality of filtered detector signals 112'. The discriminator 120 may be configured to provide the characteristic signal 114 when a condition of the discriminator 120 is met. For example, the discriminator 120 may include a peak detector 122 and a function section 124. The peak detector 122 may be configured to compare the detector signals 112 to a predetermined threshold, and the function section 124 may be configured to apply a desired function to the detector signals 112.

Figure 3:
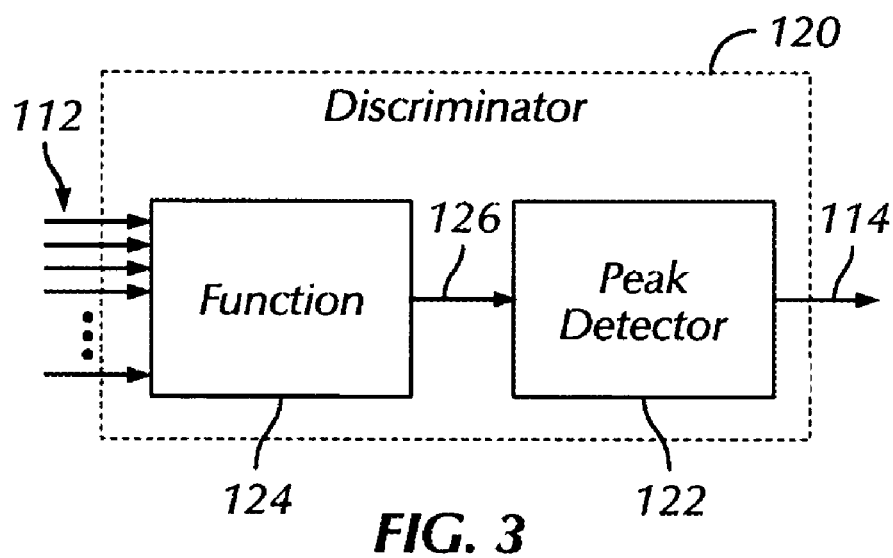
FIG. 3 is a block diagram of a discriminator utilized by a system for quantifying a characteristic of a surface of an object according to a number of embodiments.

More specifically, in embodiments as shown in FIG. 3, the function section 124 may receive the detector signals 112 and apply thereto a function, such as an arithmetic function or a conditioning function. Upon applying function, the function section 124 may then provide a functioned detector signal 126. For example, the function section 124 may utilize an algorithm that implements an additive function to the detector signals 112. In this embodiment, the function section 124 may add the detector signals 112 together, with the functioned detector signal 126 including a sum. Alternatively, the function section 124 may utilize an algorithm that implements a subtractive function, in which embodiments the functioned detector signal 126 includes a difference. In still other embodiments, the function section 124 may utilize an algorithm that implements a multiplicative function, in which embodiments the functioned detector signal 126 includes a product. Regardless of the function, after receiving the functioned detector signal 126, the peak detector 122 may determine whether the functioned detector signal 126 meets a predetermined condition or threshold. If the threshold is met, then the peak detector 122 may provide the characteristic signal 114.

Figure 4:
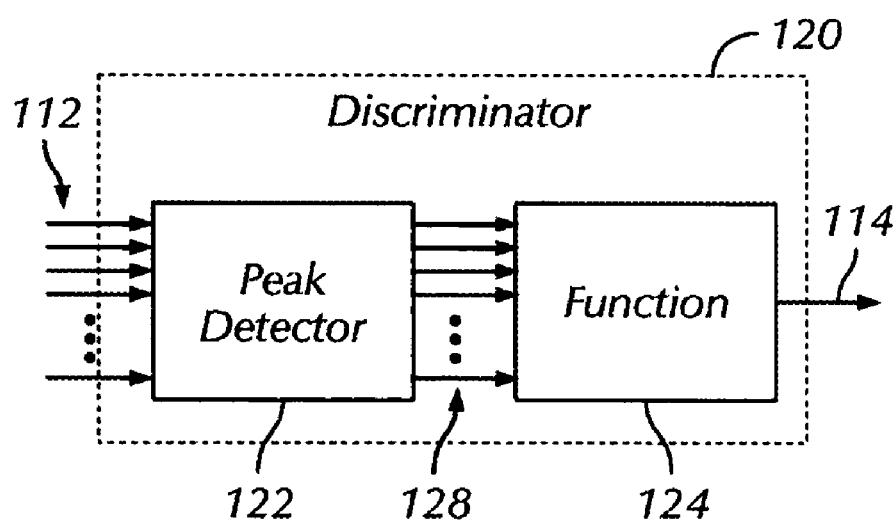
FIG. 4 is a block diagram of a discriminator according to other embodiments.

In other embodiments as represented in FIG. 4, the peak detector 122 may receive the detector signals 112 and determine whether the detector signals 112 meet a predetermined condition or threshold. If a detector signal 112 meets the threshold, then the peak detector 122 may provide a thresholded detector signal 128 to the function section 124. Upon receipt, the function section 114 may then apply a function to the thresholded detector signals 128 and, in turn, provide the characteristic signal 114 as a result of the applied function. For example, the function section 124 may utilize an algorithm that implements an AND function to the thresholded detector signals 128. Alternatively, the function section 124 may utilize an algorithm that implements a summation function to the thresholded detector signals 128.

In embodiments represented in FIGS. 3 and 4, in determining whether the detector signals 112 or 126 meet the predetermined condition, the peak detector 122 may compare each of the detector signals 112 or 126 to a predetermined threshold. More specifically, the peak detector 122 may compare to a threshold a component, such as voltage level, of the detector signals 112 or 126 that corresponds to or is indicative of a particular parameter of the received signals 110. Examples of parameters of the received signals 110 may include, but are not limited to, polarization, angular distribution, wavelength, and intensity. As a particular example, the peak detector 122 may compare a voltage level of the detector signal 112 or 126 corresponding to intensity of the received signals 110 to a threshold. If the voltage level exceeds the threshold, then the peak detector 122 may provide the characteristic signal 114 (in the embodiments of FIG. 3) or a thresholded detector signal 128 (in the embodiments of FIG. 4). Subsequent processing of the characteristic signal 114 by an output device 116 is discussed in more detail below.

Figure 5:
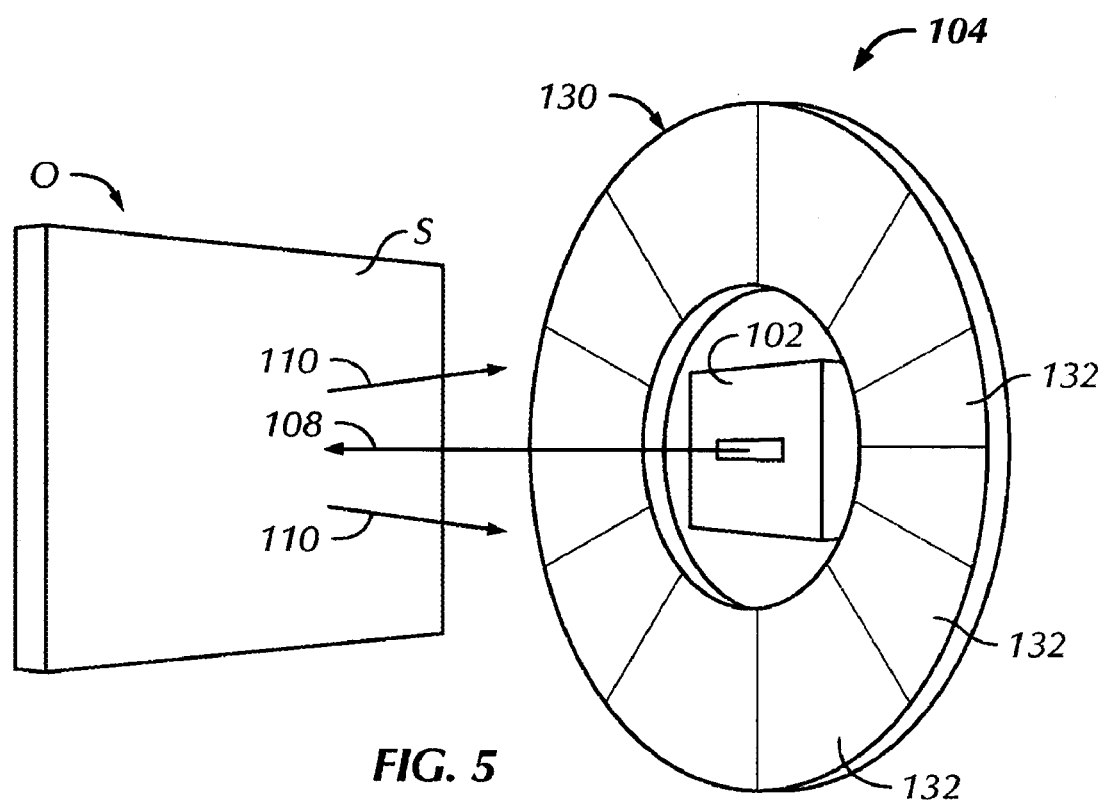
FIG. 5 illustrates a detector section of a system for quantifying a characteristic of a surface of an object according to a number of embodiments.
Figure 6:
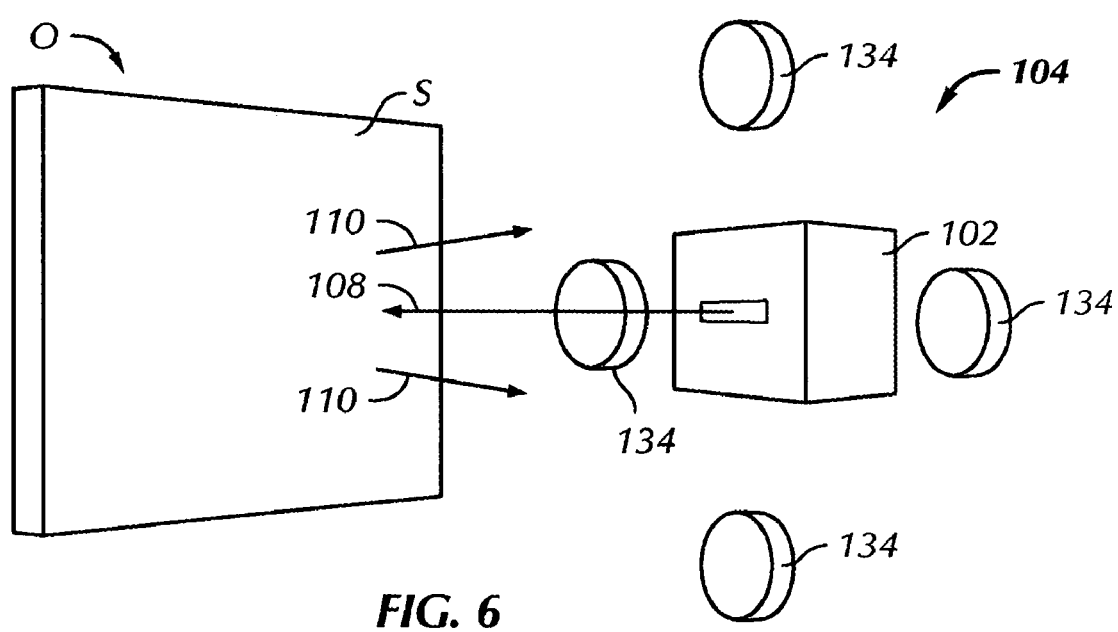
FIG. 6 illustrates a detector section according to other embodiments.

A number of embodiments of the detector section 104 are illustrated in FIGS. 5 and 6. For example, in the embodiments shown in FIG. 5, the detector section 104 may include an annular detector array 130 with a plurality of detectors 132 disposed about the energy source 102. Alternatively, in the embodiments shown in FIG. 6, the detector section 104 may include a plurality of detectors 134 disposed spatially about the energy source 102. The detections 134 may also be disposed in a spaced relationship with the surface S of the object O, for example, spatially set apart from or above the surface S.

Figure 7:
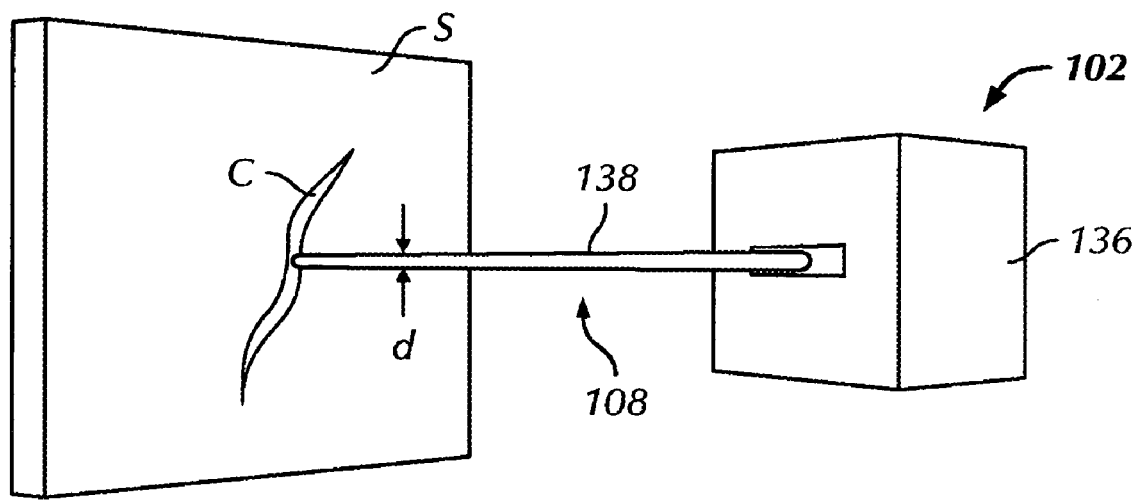
FIG. 7 illustrates an embodiment in which the size of a source beam is on the order of a defect to be characterized.

With reference to the embodiments illustrated in FIG. 7, the energy source 102 may be configured to focus the source signal 108 at or near the surface S of the object O. More specifically, the energy source 102 may include a light source 136, such as a laser or a light-emitting diode, for providing a light beam 138 which may be focused on or near the surface S. In a number of applications, the light source 136 may focus the beam 138 so as to have a dimension that has approximately the same magnitude as that of a characteristic C of the surface S to be quantified, such as a crack. For example, if the crack C has a width on the order of about 50 microns, then the light beam 138 may be focused so that at or near the surface S, a diameter d of a spot the beam 138 is on the order of about 50 microns.

The foregoing description sets forth a number of embodiments of the system 100 and its components. The following description details a number of examples of embodiments with specific applications.

EXAMPLE 1

Figure 8:
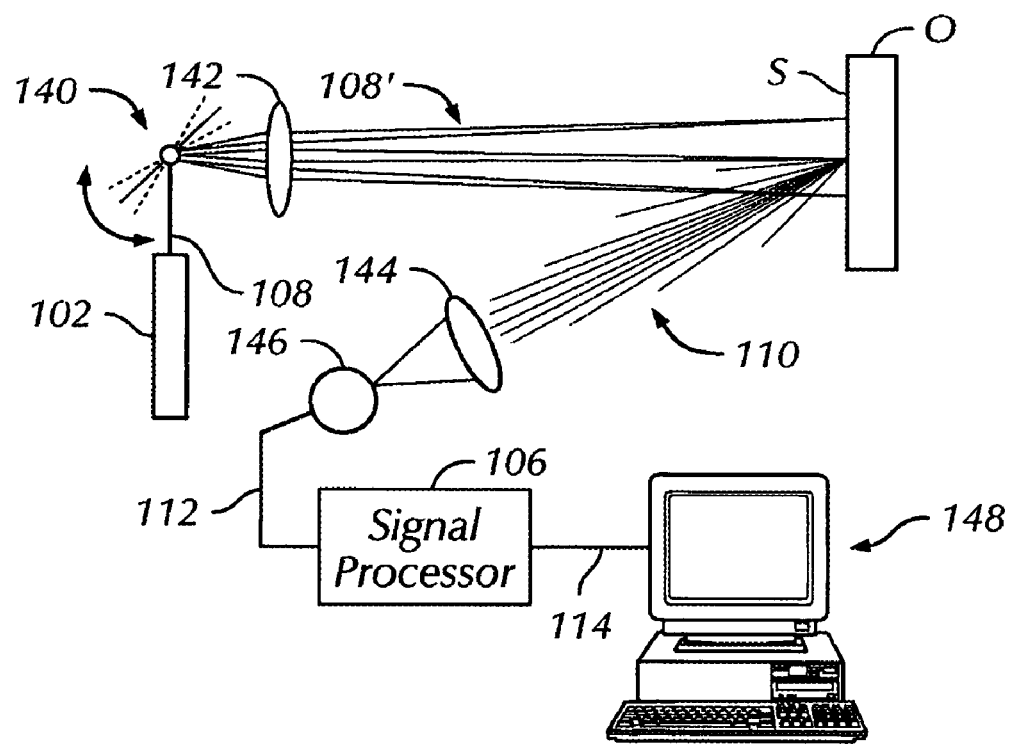
FIG. 8 illustrates a scattered light scanning system for local defect detection.

An example of a scattered light scanning system 100 is shown in FIG. 8. The energy source 102 includes a laser, such as a NEX model GLG5261 10 mW helium-neon laser. The beam 108 is directed through a series of stationary mirrors (not shown) and onto a scanner 140, such as a Newport model 425 rotating octagonal mirror. The mirror 140 rotates at a rate that produces 1,250 sweeps of the laser beam 108 per second over the specimen O. The beam 108 is directed by mirrors (not shown) to sweep vertically, while the octagonal mirror 140 rotates in a horizontal plane. A linear trace of 75 mm at the focal distance of a lens 142 of approximately 300 mm is covered by the scanning beam 108'. The surface area of the specimen O to be monitored is centered in the middle of the beam sweep, as close to the focal distance as possible. The beam spot width on the specimen surface S is approximately 60 μm.

The beam 108' is reflected specularly from smooth areas of the surface S and scattered from rough areas of the surface S after the laser beam 108' hits the surface S of the specimen O, which reflected and scattered beams are indicated by 110. A second lens 144 and the fiber optic cable (not shown) collect the scattered light 110. The collected light is detected by a photo detector (PD) 146, which produces an electrical output 112 proportional to the amount of light received.

The amplified signal 112 from the PD 146 passes through a signal processing system 106, which distinguishes defect detection using a threshold scattered-light intensity level algorithm. Setting of threshold level is based on the intensity of scattered light from an undamaged specimen area. The PD output 112 is amplified and processed through an SRS model SR 240 fast preamplifier and an Insitec signal processor. The output is then converted into a rate between adjustable limits by an Ortec Model 550 threshold/window device and an Ortec Model 449 rate meter. The processed signal 114 is then fed to a computer 148 for display and analysis.

The detector signal 112 is amplified, processed, and converted into a rate designated as the "defect frequency" which is used as a direct indication of the light scattering signature of a location on the scanned surface. The beam 108 produces a defect frequency count each time it encounters any surface perturbation resulting from localized fatigue deformation that scatters light above the predetermined threshold. The defect frequency measured is governed by the nature of the specimen surface S, the location of the light collecting lens 144, and the settings on the signal processing equipment 106. Defect frequency can be related to surface changes leading to crack initiation, and can also be used to determine crack density if multiple cracks are nucleated at the surface S. Accordingly, the characteristic signal 114 may be processed by the computer 148, for example, to determine a failure precursor of the specimen O, in performing a damage prognosis of the specimen O, in performing a remaining-life prognosis of the specimen O.

The rotating mirror 140 and laser 102 may be fixed to a portable deck, which can be moved as necessary to align with the specimen O. A clamp (not shown) holds the light collector 144, which allows it to be positioned for different detection modes.

EXAMPLE 2

Figure 9:
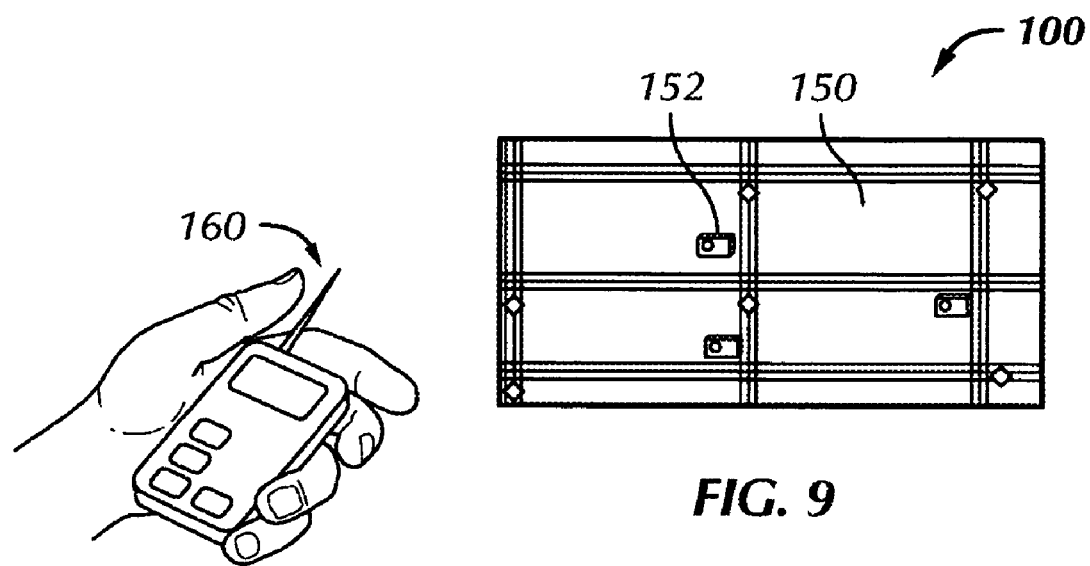
FIG. 9 illustrates an example of a fatigue inspection in which compact optical measuring sensors are attached to the airplane skin interface with a palmtop computer to catalog the measurements.
Figure 10:
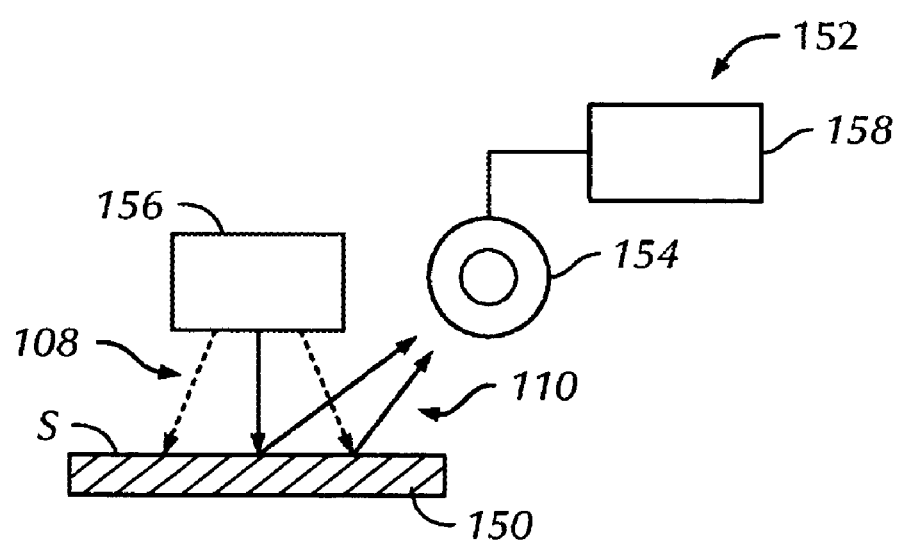
FIG. 10 illustrates source and detector sections of the example of FIG. 9.

FIG. 9 shows an embodiment for monitoring surface condition of an aircraft component 150 in situ. As shown in FIG. 10, the source 102 and the detector section 104 are implemented into a sensor 152 that includes a detector 154 and a small diode laser (or LED) 156. The detector 154 is a small rugged detector attached directly to the component 150 under inspection. The laser 156 emits a beam 108 that is focused and scanned over a region of interrogation of the component 150. The scattered light 110 is then collected by an optical element (not shown), fed into the detector 154, and analyzed by an embedded processor 158 with on-board memory. The characteristics of the scattered light 110 include several types of information that can be used to assess the condition of the surface S of the component 150.

One change occurs when the spot of the scanned beam 108 crosses a microcrack. The light diffracted from a microcrack is typically concentrated along a line that is normal to the crack direction. This property enables the light diffracted and/or scattered from the defect precursor to be separated from the light scattered from typical roughness features on the surface S.

Another change in the behavior of the scattered light 110 occurs as grain boundaries deform with change in residual stress. The system 100 that tracks and analyzes these changes in the behavior of the scattered light 110 can provide a warning of potential catastrophic failure of the component 150.

In a number of embodiments, the sensor 152 may be networked to a palmtop 160 or laptop computer through a wireless Ethernet connection. Because of exceptionally low power consumption, the sensor 152 has a long life and can operate as a leave-in-place or in situ module. In other embodiments, the sensor 152 may be integrated in an opto-MEMS configuration that significantly reduces its physical dimensions and weight.

Measurement of fatigue damage is important in all forms of machinery and critical in the area of aircraft safety. The system 100 provides an useful and cost-effective diagnostics tool that can be used by aircraft maintenance centers. In addition, the system 100 is applicable in the mechanical measurement and test community, in particular for commercial and military aircraft inspection.

Structural integrity and early defect detection are key factors in a variety of industries, in particular for airframe manufacturers and in the maintenance of deployed aircraft. Conventional instruments for non-destructive interrogation are bulky, expensive, time consuming, and require high qualification of the maintenance team. Some non-destructive interrogation methods are able to detect and quantify specific defects (e.g., corrosion) but are not practical for field application, where time, cost, and complexity are critical factors.

Vital information on the conditions of the component 150 under inspection can be obtained from a direct characterization of dislocations or surface variations, which conventionally is only possible under the high magnification of a scanning electron microscope (SEM). Due to its bulky and fragile nature, the SEM-technique is clearly not suitable as a portable field inspection instrument. Optical detection of precursor dislocation structures prior to crack formation is generally difficult. However, the initial formation and movement of dislocations to form slipband structures, which reduces the surface residual stress, has been observed with SEMs and atomic force microscopes (AFMs) in both nickel alloy and aluminum. Also, a laser light scattering technique was shown to efficiently detect not only micro-cracks, but also a change in the surface residual stress for extruded wires that were subject to high cycle fatigue testing and corrosion. The premise of the concept is that statistical evaluation of such changes occurring in the microscopic surface profile can be used as a direct indicator of dislocation formation and movement within the first 50% of fatigue life.

EXAMPLE 3

Figure 11:
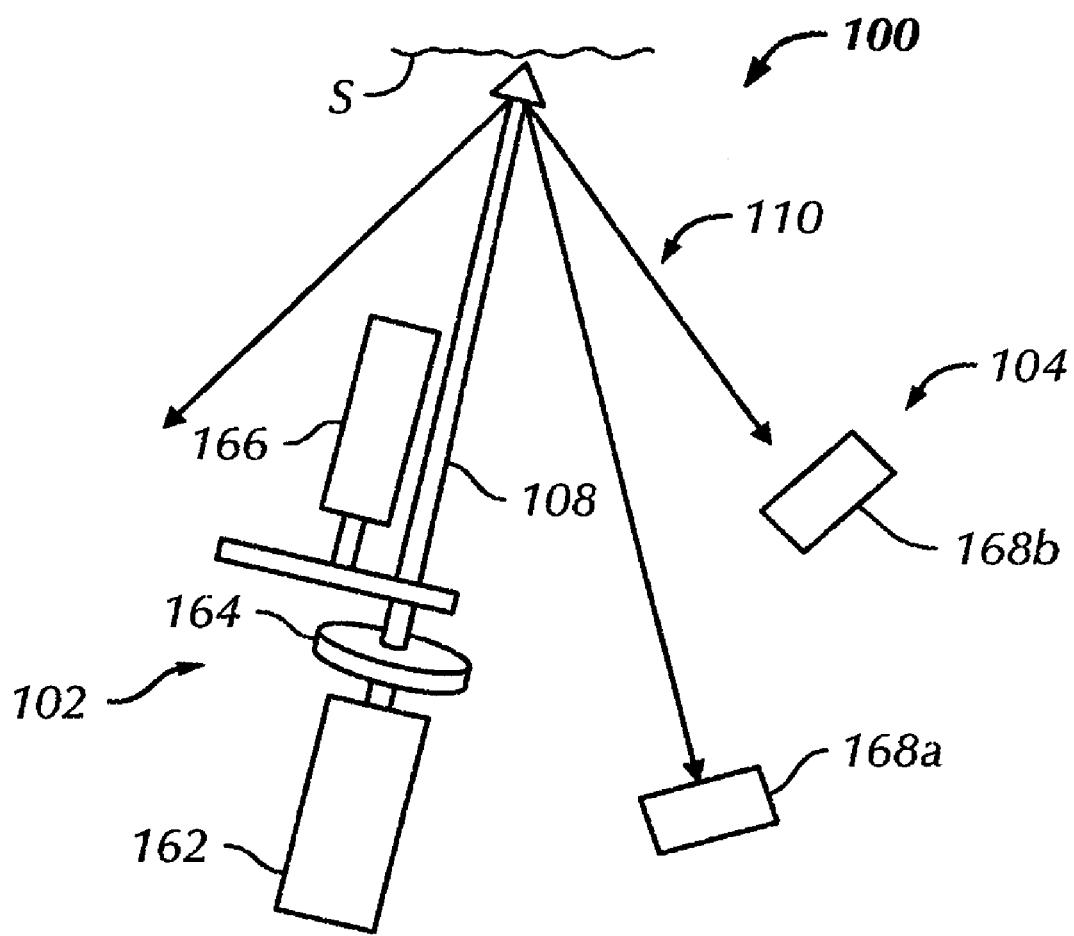
FIG. 11 illustrates an example of a surface scanning configuration used to determine residual stress relaxation in wires.

FIG. 11 illustrates an example of a system 100 for monitoring scattered light. Either the specular component or diffuse component of light, or both, can be detected. The energy source 102 includes a laser 162, a lens 164, and a scanner 166, and the detector section 104 includes a plurality of detectors 168a, 168b, . . . . Any number of detectors 168 may be positioned to enhance the reception of specular components of the reflected light 110, as represented by detector 168a, and any number of detectors 168 may be positioned to enhance the reception of diffuse components of the reflected light 110, as represented by detector 168b.

As the laser 162 is scanned over the surface, changes in light levels are produced by roughness of the surface S. Cracks on the order of the spot size (as mentioned above) produce a significant change in the detected signal 110; however, even sub-micron features can be detected. Using threshold circuitry 106, the scanned signal can be converted into a parameter known as defect frequency $F_d$ given by $$F_d = N/v \tag{1}$$

where N is the number of defects per linear dimension and v is the scanning velocity. The defect frequency can be used to track the growth of cracks as well as the change in surface roughness that occurs during initial fatigue damage. Thus, the system 100 utilizes the defect frequency $F_d$ as a useful measurement during all stages of the fatigue cycle.

Figure 12A:
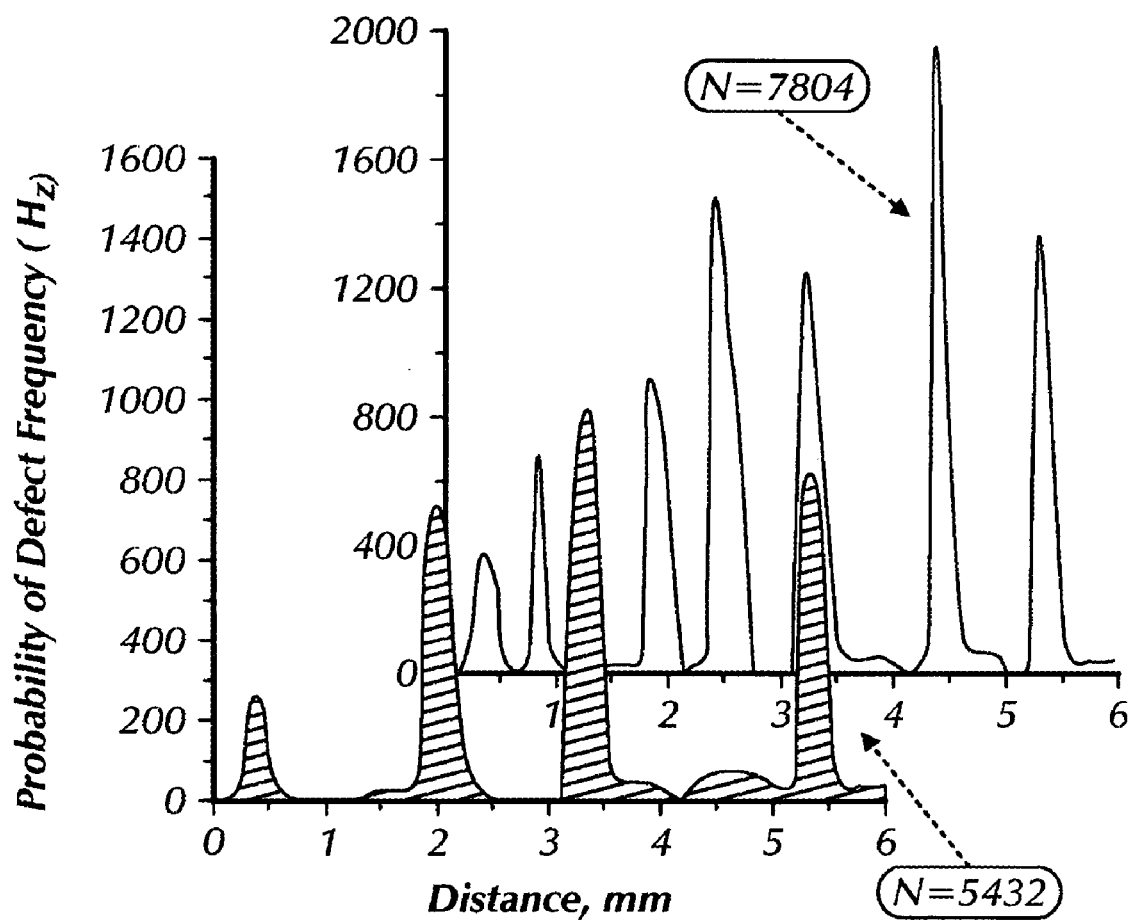
FIG. 12A illustrates an example of crack distribution along the test section at two different cycle numbers, in which N=5432 and N=7804.
Figure 12B:
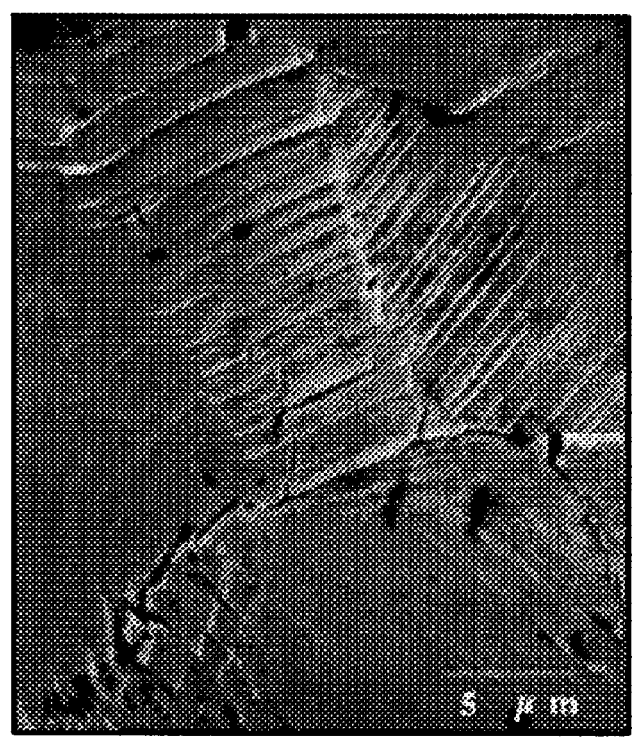
FIG. 12B illustrates SEM micrograph of the surface of FIG. 12A.

A typical example of test results utilizing the system 100 of FIG. 11 is shown in FIG. 12. FIG. 12A presents the raw signal for two different cycling states. Clearly, the increased damage is quantified. The SEM micrograph produced from a polymer replica of the same surface clearly illustrates the crack formation in FIG. 12B. FIG. 12B shows a surface after cyclic loading created damage in the test sample. The presence of striations on the fracture surface indicates that fatigue failure occurred. Cracks associated with fatigue failure typically initiate or nucleate on the surface of a component at a point of stress concentration. Crack nucleation sites include scratches, sharp fillets, keyways, threads, and dents. The direction of crack motion is very nearly perpendicular to the direction of the applied tensile stress and yield.

To characterize crack formation and material response to a cyclic load, the parameter $f_d$, which is called the Defect Probability Frequency (DPF), is introduced. The DPF is defined as the number of light intensity excursions through a pre-selected threshold level per second. A mean DPR, $\bar{f}_d$, can also be determined for a specimen surface which is the spatial average of $f_d$ over the inspection length for a given number of cycles. The change in these two parameters over the course of a low cycle fatigue (LCF) experiment is discussed in the following. A typical plot of DPF versus number of cycles is shown in FIG. 13.

Figure 13:
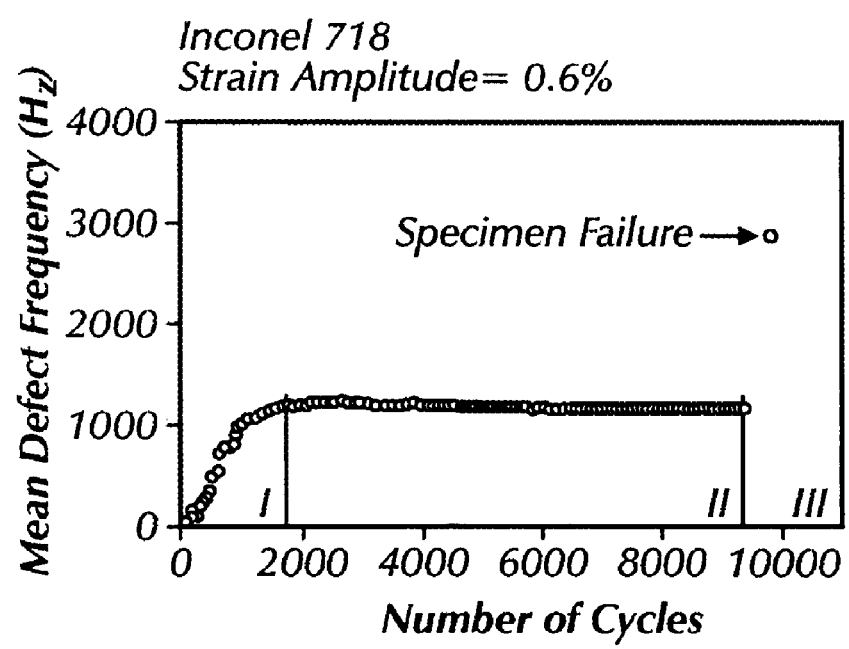
FIG. 13 illustrates a plot of mean defect frequency versus number of cycles over the entire life of a specimen.

FIG. 13 illustrates a typical plot of mean defect frequency versus number of cycles over the entire life of a specimen. As shown, the DPF, $\bar{f}_d$, versus cycle number during the specimen life has three characteristic stages: (1) a rapid initial increase, (2) a plateau that covers most of the life of the specimen, and (3) a final sudden increase immediately preceding specimen failure. Thus, a characterization based on this transition is possible and is potentially useful since it occurs long before the overall strength of the specimen is significantly affected by fatigue damage. The relationship between $\bar{f}_d$ and the development of LCF damage observed on surface replicas can be used to quantify and track the fatigue state of the aerospace components.

The relationship between cyclic loading and a decrease in residual stress has been observed and reported by many researchers. Optical visualization of precursor dislocation structures and micro-cracks prior to crack formation is generally not possible; however, in materials that have moderate to high surface residual stresses, the initial formation and movement of dislocations to form slipband structures tend to reduce the surface residual stress. Analysis of the light scattered from a surface enables detecting this change in surface residual stress. This detection was facilitated by the significant change in surface roughness that results from the relaxation of surface residual stresses and the sensitivity of the speckle pattern to such changes.

Figure 14A:
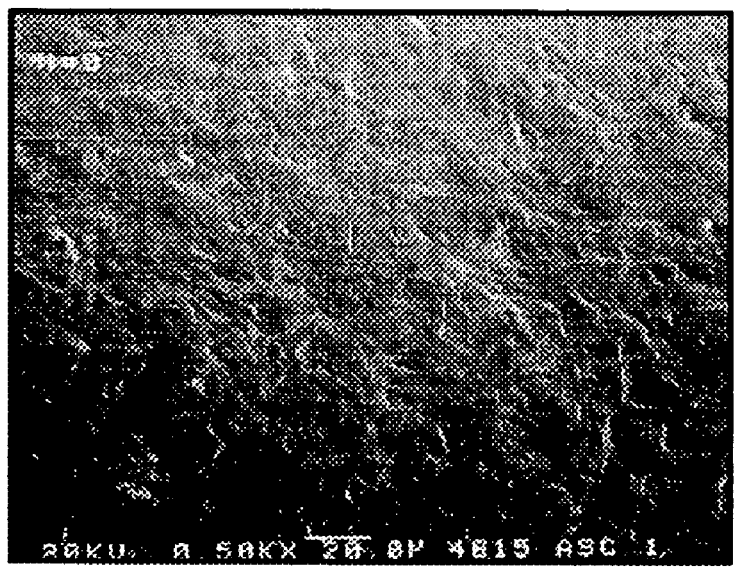
FIGS. 14A and 14B respectively illustrate a SEM micrograph of the "as-drawn" surface of an wire specimen prior to fatigue testing and (b) the surface of a wire specimen after 10,000 cycles of fatigue loading (R=0.1)
Figure 14B:
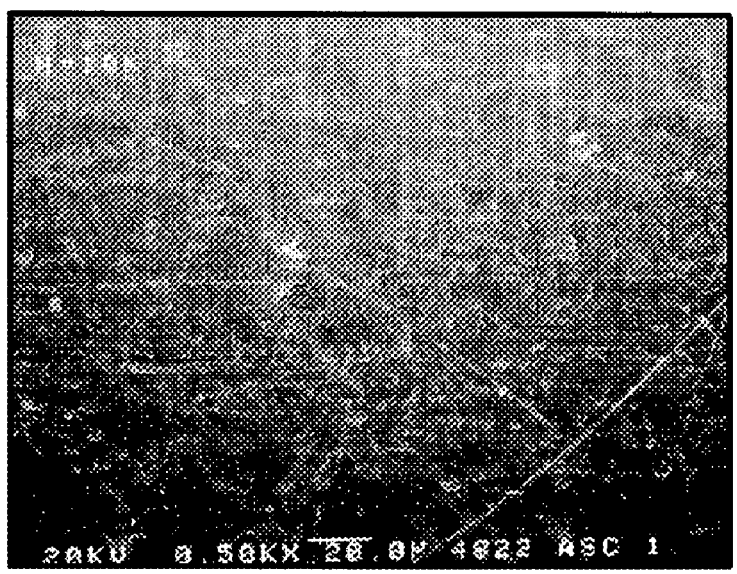
Figure 15:
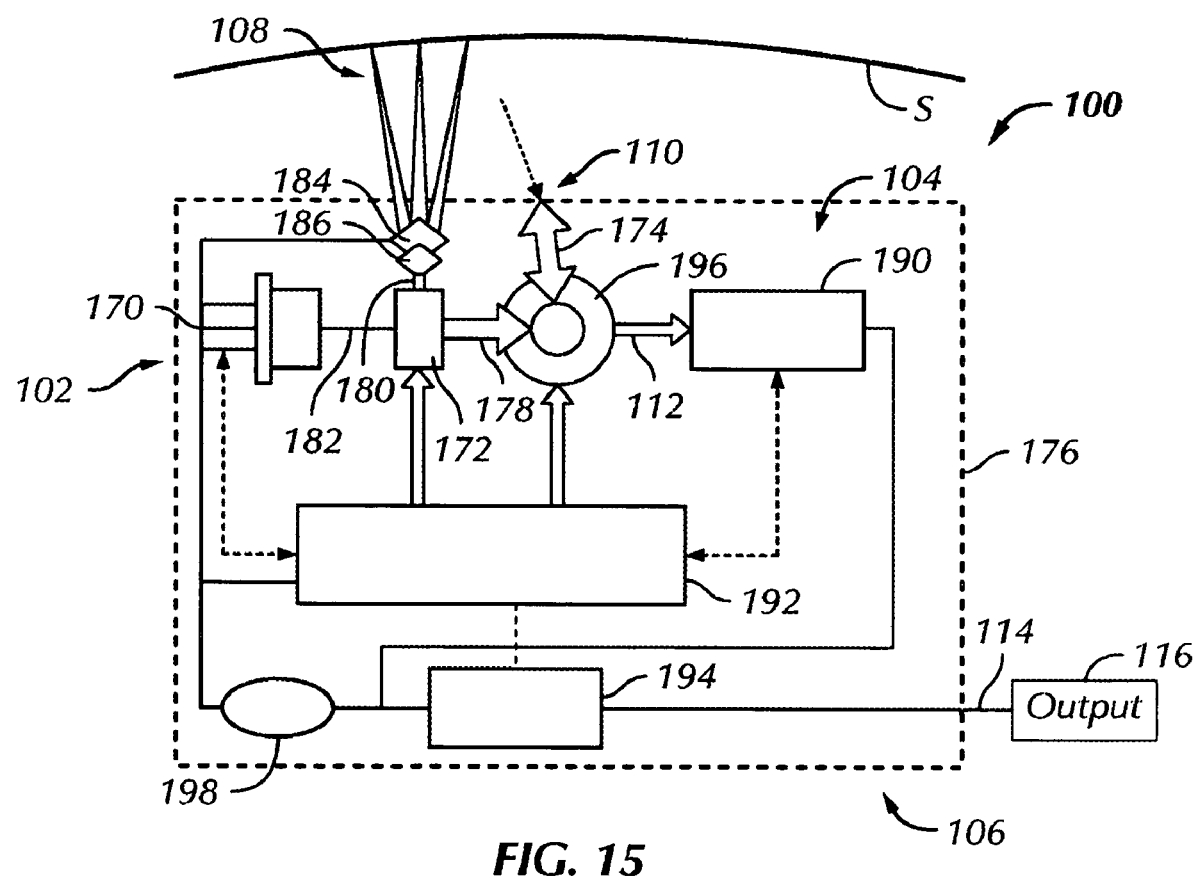
FIG. 15 illustrates an example of a system implemented as an in situ sensor.

FIGS. 14A and 14B are SEM micrographs of surface topographies of an "as-drawn" wire sample before and after testing under high cycle fatigue conditions, respectively. This observed change in topography results in a detectable (up to 90%) decrease in the intensity of laser light scattered from the surface long before crack initiation. Thus, residual stress relaxation under fatigue conditions can give rise to changes in surface topography that are detectable using the system 100 of the invention.

Although the relationship between fatigue damage and surface residual stress has been identified in the art, it has not been exploited as a measurement tool for early fatigue damage. It is well known that the effects of fatigue manifest themselves primarily at the surface. While the roughness of a surface is highly dependent on the type of finishing used, the changes in the roughness are related to the relaxation of residual stresses and the formation of the cracks. Statistical evaluation of the surface roughness by the system 100 of the present invention provides an assessment that is independent of exact measurement location. Fatigue damage is monitored throughout the component lifetime by the present invention through this statistical evaluation of the surface roughness.

EXAMPLE 4

In a number of embodiments, the system 100 may include may be implemented in an opto-MEMS format assembled with a light source such as a small diode laser 170, an optical beam splitter 172, and a detector 174. In this embodiment, the type of light source utilized in the system 100 may be determined by an analysis of the sensitivity of the system 100 and signal-to-noise ratio, in combination with the modeling data of the optical signal delivery efficiency.

One element of the system analysis and optimization is related to the design of the optical assembly 102, a MEMS-type module for beam scanning, and microlens for scattered light detection. The system 100 may include a housing 176 in which that compact diode laser or LED 170 and other components are placed. The optical beam-splitter 172 forms a reference channel 178 and a signal channel 180. The reference channel 178 is defined by a portion of beam 182 that is transmitted directly to the photo receiver or detector 174 downstream of the beam-splitter 172. The reference channel 178 is housed within the housing 176 of the system 100 and is utilized for system calibration. The signal channel 180 is defined as a portion of beam 182 that is transmitted to the surface S through an attached MEMS-type beam controller and scanning element 184.

In operation, the scanning element 184 scans the beam 108 that is focused by a microlens 186 on the surface S of a target. The scattered light 110 is then collected by an optical element and is detected by the photo receiver 174 which generates a detector signal 112. The process section 106 may include a rate-counter 190 that counts the number of scattered light intensity excursions beyond a preset threshold level. A driver 192 may operate components of the source section 102 and the detector section 104 by collecting and processing data from the photo receiver 174 and comparing such date with relevant data stored in memory. An interface 194 conveys information in the characteristic signal 114 to an output device 116 for a user. The process section 106 may include a controller 196 to monitor the operation of the system 100. Power may be supplied by a battery 198.

The comparison of the data from the reference and signal channels 178 and 180 allows for detection of the transformation in the scattering characteristics of the surface S under inspection by measuring the number of splashes that are related to crack formation. Collected and processed information may be stored in an on-board memory section (not shown) of the system 100 and then wirelessly transferred to an output device 116 such as a palmtop-type of computer, for example, when requested by a maintenance crew of an aircraft. The data transfer may be performed using the IEEE 802.11b standard, infrared Bluetooth standard, and so on.

To reduce power consumption, the system 100 may operate in two distinct modes: a low-power, standby mode (most of the time) and an active mode while scanning, reading data, processing, and transferring the data. In standby mode, only the data interface 194 need be operating while waiting for a scan request from the systems internal program or operator.

The beam scanner 184 and the light collector of the receiver 174 may be analyzed to optimize modeling. A number of components may be selected for optimal operation of the system 100, such as the selection of the light source (e.g., coherent versus incoherent); a MEMS-type laser beam scanning system with a capability to vary the scan-line width, length, and spatial orientation; and an optical system for scattered light collection with maximal efficiency to maintain the detectable power balance in the returned signal.

The operational features of the measuring system 100 are robust and reliable and allow the system 100 to be configured as a sensor that is essentially a leave-in-place or in situ detector. Once the system 100 is ON and the source signal 108 is transmitted to the surface S of the sample, the scanned beam 108 produces a signal based on the light scattered from the surface S. Alignment is not necessary for system operation, as data retrieval is based on a comparison of the intensity of the reference channel 178 and the signal channel 180, which may be adjusted. This methodology ensures the reliability of the system operation. Thus, the system 100 embodied as such a sensor module is robust, compact, and reliable.

EXAMPLE 5

Figure 16:
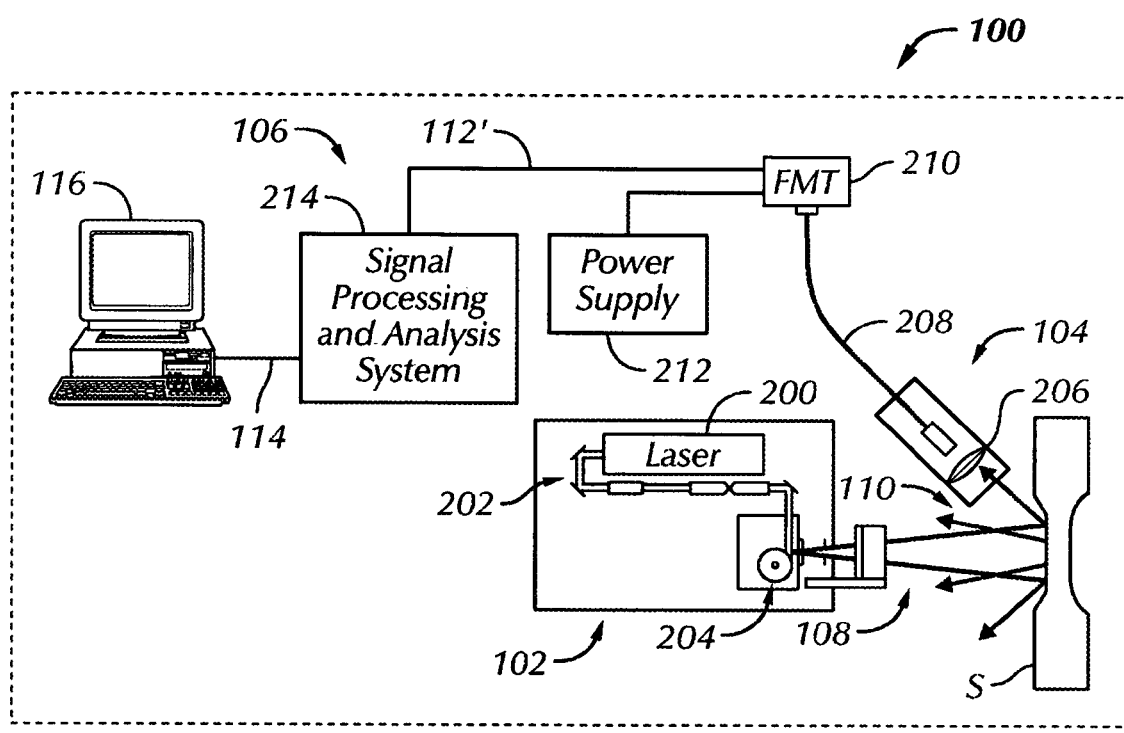
FIG. 16 illustrates an example of a laser scanning detection system.

FIG. 16 illustrates another embodiment of the system 100 which may be utilized as an experimental setup for performing micro-crack detection. The source section 102 may include a 10 mW helium-neon laser 100 for generating a beam that passes through a set of mirrors 202 and is then directed onto a rotating octagonal mirror 204. The mirror 204 may rotate at a rate of about 1,250 sweeps per second over the surface S of a specimen. A linear drive 205 may be utilized so that the scanning beam 108 covers a linear trace of about 75 mm. The specimen area to be monitored may be centered in the middle of the beam sweep close to the focal plane. The beam spot width on the specimen may be approximately 60 microns.

The detector section 104 or light collection module may include a lens 206 and an optical fiber 208 for collecting the light 110 that is scattered off the surface S and delivering the collected light to a photo detector (PD) 210 with a power supply 212. The PD 210 produces an electrical output proportional to the amount of light received. The amplified signal 112' from the PD 210 passes through a signal processing system 214 of the process section 106. The signal processing system 214 may determine defect detection by using a predetermined scattered light intensity threshold that is based on the intensity of scattered light from an undamaged specimen. The PD output 112 may be converted into a processed signal 114 that includes a rate, with the processed signal 114 then being fed into a microcomputer 116 for display and analysis.

In this embodiment, the output signal 114 is not an image. The data of the signal 114 are used as a direct indication of the light scattering signature of the surface S. The electrical signal 112' is amplified, processed, and converted into a rate designated as defect frequency $F_d$ (as mentioned above). The beam 108 produces a count when a perturbation such as a slip band or microcrack is encountered on the surface S. The defect frequency $F_d$ observed is determined by the nature of the surface S of the specimen, the location of the light collector 206, and the settings on the signal processing system 214. Defect frequency $F_d$ can be related to surface changes leading to crack initiation, and can also be used to determine crack density if multiple cracks are nucleated at the surface S.

In an experimental procedure, laser scanning was performed during periodic interruptions of the tension-going part of the loading cycle at approximately zero strain corresponding to a considerable stress in tension due to the hysteresis in the stress-strain response. Interruption at this point in the loading cycle assures that any micro-cracks that form are held open during the laser scanning. An automated servo-hydraulic MTS model 810 was used to determine the fatigue properties of the sample. A LabView program was used for data acquisition and control.

EXAMPLE 6

An Application to Turbine Blades

Fatigue damage on the surface of turbine blade/rotor sections was monitored using the present invention. Substantially greater values of the parameter defined as defect probability were observed in higher stressed regions of the surface by scanning the sample during interruptions of the cyclic loading. Furthermore, the average defect frequency determined during cycling for these higher stresses regions gradually increased with load cycling. Surface replications with acetate film also made during the interruptions in cyclic loading revealed that the increase in defect frequency corresponds to the formation of grooves in the regions of highest stress. Residual stress measurements for tested and untested samples indicate that the grooves were not associated with a relaxation of residual stresses. Rather, they appear to have resulted from localized slip processes along the grain boundaries. Following testing, the presence of these grooves was confirmed by direct SEM of the sample surface.

The physical nature of the interdependence between surface defects and internal damage is determined by the nature of mechanical disintegration. The durability of metallic components is determined by numerous conditions and depends on the internal structure realignment that occurs under mechanical loading. This internal reordering is reflected by the formation of surface cracks. The development of internal structure realignment leads to an increase in the concentration of the surface defects. The relationship between internal object condition and its surface condition (concentration of the surface defects) is nonlinear and depends on the various factors, in particular, the object's shape. Now this relationship in the general case is unknown, but numerous observations show that for a given metallic object there is the critical concentration of surface cracks, which excess leads to buckling and mechanical failure.

The derivative of the received scattered light is described by the sum of the pulse functions centered on the boundaries of the surface defect. This means that measuring distances between maxima of the pulse function shows us the defect size if the defect size is greater than the order of the spot size. If this condition does not hold, the resolution limit will be equal to the width of the pulse function. Nevertheless on the basis of the above-mentioned measurement, a conclusion can still be made about the presence of small defects and their concentration. This information is important because for the mechanical failure of a given specimen in a given configuration, there is a threshold concentration of surface defects of a certain size. This concentration reflects the critical reordering of the internal structure of a specimen.

Those skilled in the art will understand that the preceding embodiments of the present invention provide the foundation for numerous alternatives and modifications thereto. These other modifications are also within the scope of the present invention. Accordingly, the present invention is not limited to that precisely as shown and described in the present invention.

What is claimed is:

1. A system for quantifying an evolution an characteristic of a surface of an object, the system comprising:
    an energy source for transmitting a source signal over time to a surface of an object for specular reflection or scattering;
    a detector section for receiving a received signal from the surface and for providing a detector signal indicative of the received signal, the detector section receives a plurality of received signals and provides a corresponding plurality of detector signals;
    a processor for receiving the detector signal from the detector section, the processor for applying an algorithm to the detector signal to quantify at least one of a temporal and a spatial change in a characteristic of the surface, the processor applying the algorithm to the plurality of detector signals, the processor includes a peak detector for comparing each of the detector signals to a threshold and providing a thresholded detector signal when a respective one of the detector signals meets the threshold, the processor providing a characteristic signal when a condition of the peak detector is met, the processor applying a summation function to the threshold detector signals and providing the characteristic signal when the result of the summation function meets the threshold; and
    a computer for receiving the characteristic signal from the processor and for processing the characteristic signal, the computer processing the characteristic signal to at least one of determine a failure precursor, perform a damage prognosis, and perform a remaining-life prognosis.

2. The system of claim 1 wherein the characteristic of the surface that the processor quantifies is selected from a group consisting of a defect, a slipband, a crack, a microcrack, a pit, a damage feature, corrosion, erosion, a contour change, an impact crater, and a change in residual stress.

3. The system of claim 1 wherein the energy source and the detector section are installed in situ with respect to the object.

4. The system of claim 3, wherein the energy source and the detector section are installed to provide at least one of continuous and discrete monitoring of the object over a predetermined time period.

5. The system of claim 4, wherein the predetermined time period includes a span of at least a plurality of seconds to a plurality of years.

6. The system of claim 3, wherein the object is measured to quantify at least one of temporal changes and spatial changes in the characteristic of the surface of the object.

7. The system of claim 6, wherein the temporal changes indicate at least one of fatigue damage and surface residual stress.

8. The system of claim 7, wherein the fatigue damage is monitored throughout the component lifetime.

9. The system of claim 7, wherein fatigue damage is monitored using statistical evaluation of the surface roughness.

10. The system of claim 3, wherein the object includes an aircraft component disposed in an aircraft, the energy source and the detector section being installed in the aircraft.

11. The system of claim 10, wherein the aircraft component is a turbine rotor.

12. The system of claim 10, wherein changes in the aircraft component are related to at least one of fatigue loading conditions, impending crack formation, and foreign object damage.

13. The system of claim 1, wherein the processor determines which of the detector signals are relevant based on a parameter of the detected signals.

14. The system of claim 13 wherein the detector signals have a polarization, and the processor utilizes polarization of the detector signals to determine relevancy.

15. The system of claim 13 wherein the detector signals have an incident angle, and the processor utilizes the incident angle of the detector signals to determine relevancy.

16. The system of claim 13 wherein the detector signals have a wavelength, and the processor utilizes the wavelength of the detector signals to determine relevancy.

17. The system of claim 1 wherein the algorithm includes an additive function for adding the detector signals to provide a sum;
    the peak detector providing the characteristic signal when the sum meets a threshold.

18. The system of claim 1 wherein the algorithm includes an subtractive function for subtracting the detector signals to provide a difference;
    the peak detector providing the characteristic signal when the difference meets a threshold.

19. The system of claim 1 wherein the algorithm includes a multiplicative function for multiplying the detector signals to provide a product;
    the peak detector providing the characteristic signal when the product meets a threshold.

20. The system of claim 1 wherein the processor applies an AND function to the thresholded detector signals and provide the characteristic signal as a result of the AND function.

21. The system of claim 1 wherein the detector section includes a plurality of detectors disposed spatially about the energy source.

22. The system of claim 1 wherein the detector section includes a plurality of detectors disposed spatially above the surface of the object.

23. The system of claim 1 wherein the detector section includes an annular detector disposed about the energy source.

24. The system of claim 1 wherein the energy source includes a light source for providing a source signal tat is focused on or near the surface and has a dimension of approximately the same magnitude as that of the characteristic of the surface to be quantified.

25. A method for quantifying an evolution of a characteristic of a surface of an object, the method comprising:
    transmitting a source signal over time to a surface of an object for specular reflection or scattering;
    detecting a received signal from the surface, the detecting step including receiving a plurality of received signals and providing a corresponding plurality of detector signals; and
    processing a detector signal indicative of the received signal by applying an algorithm to the detector signal to quantify at least one of a temporal and a spatial change in a characteristic of the surface, the processing step includes processing the plurality of detector signals by applying the algorithm, the processing step includes providing a characteristic signal when at least one detector signal meets a condition, the processing step includes processing the characteristic signal to at least one of determine a failure precursor, determine a damage prognosis, and determine a remaining-life prognosis, wherein the processing includes comparing each of the detector signals to a threshold and providing a thresholded detector signal when a respective one of the detector signal meets the threshold and applying a summation function to the threshold detector signals; and providing a characteristic signal when at least one of the detector signals meets a condition and providing the characteristic signal when the result of the summation function meets the threshold.

26. The method of claim 25 wherein the processing step includes processing the detector signal to quantify a characteristic of the surface selected from a group consisting of a defect, a slipband, a crack, a pit, a contour change, an impact crater, and a change in residual stress.

27. The method of claim 25 wherein the processing step includes determining which of the detector signals are relevant based on a parameter of the detected signals.

28. The method of claim 26 wherein the processing step includes adding the detector signals to yield a sum, the providing step including providing the characteristic signal when the sum meets a threshold.

29. The method of claim 26 wherein the processing step includes subtracting the detector signals to yield a difference, the providing step including providing the characteristic signal when the difference meets the threshold.

30. The method of claim 26 wherein the processing step includes multiplying the detector signals to yield a product, the providing step including providing the characteristic signal when the product meets a threshold.

31. The method of claim 26 wherein the processing step further includes applying an AND function to the thresholded detector signals, the providing step including providing the characteristic signal as a result of the AND function.

32. The method of claim 26 wherein the transmitting step includes focusing a light beam on or near the surface, the light beam having a dimension that is approximately the same magnitude as that of the characteristic of the surface to be quantified.

* * * * *